United States Patent [19]

Sohda et al.

[11] Patent Number: 5,296,499
[45] Date of Patent: Mar. 22, 1994

[54] INDOLE DERIVATIVES, THEIR PRODUCTION AND USE

[75] Inventors: Takashi Sohda, Takatsuki; Iwao Yamazaki, Takarazuka; Noriaki Kawamura, Suita, all of Japan

[73] Assignee: Takeda Chemical Industries, Ltd., Osaka, Japan

[21] Appl. No.: 963,252

[22] Filed: Oct. 19, 1992

Related U.S. Application Data

[63] Continuation of Ser. No. 674,214, Mar. 25, 1991, abandoned.

[30] Foreign Application Priority Data

Mar. 26, 1990 [JP] Japan .................... 2-78494

[51] Int. Cl.$^5$ ................. C07D 209/18; A61K 31/405
[52] U.S. Cl. ..................... 514/419; 544/279; 544/336; 544/333; 544/238; 544/212; 544/62; 544/143; 544/373; 548/364.7; 548/311.7; 548/312.1; 548/113; 548/364.4; 548/266.4
[58] Field of Search ............... 548/506, 507, 509, 510, 548/254, 134, 136, 374, 336, 181, 235, 247, 430, 465, 255, 262.2, 143, 131; 514/415, 419, 364, 363, 362, 301, 314, 358, 381, 374, 378, 372, 365, 397, 406, 253, 269, 334, 241, 235.2, 325.2, 323, 411; 544/279, 143, 238, 336, 62, 373, 212, 333; 546/122, 117, 114, 273, 201

[56] References Cited

U.S. PATENT DOCUMENTS

4,014,883 3/1977 Fryer et al. .................. 260/288 CF

FOREIGN PATENT DOCUMENTS

68563 1/1983 European Pat. Off. .

OTHER PUBLICATIONS

Raisz, "Bone Resorption in Tissue Culture," *J. Clin. Invest.*, vol. 44, No. 1, 1965, pp. 103–116.
European Search Report (1992).
Shigeho INABA et al., "Benzodiazepines. IV. A New Synthesis of 1-Diethylaminoethyl-substituted 1,4-Benzodiazepin-2-ones". *Chem. Pharm. Bull.*, vol. 19, No. 2, pp. 263–272 (1971).
Gordon N. Walker et al., "Novel Syntheses of 1,4-Benzodiazepines, Isoindolo[2,1-d][1,4]benzodiazepines, Isoindolo[1,2-a][benzazepines, and etc." *J. Org. Chem.*, vol. 37, No. 24, pp. 3755–3770 (1972).
Armin Walser et al., "The Synthesis and Transformations of Some 3-Chloro- and 3-Nitroindolenines", *J. Org. Chem.*, vol. 38, No. 18, pp. 3077–3084 (1973).

*Primary Examiner*—Robert T. Bond
*Attorney, Agent, or Firm*—Wegner, Cantor, Mueller & Player

[57] ABSTRACT

An agent for inhibiting bone resorption comprising an indole derivative of the formula (I):

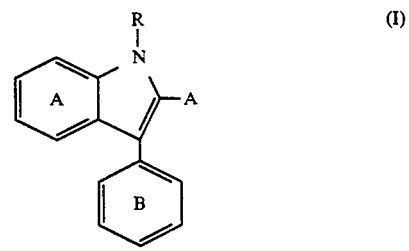

wherein each ring of A and B is optionally substituted, R is a hydrogen atom, a lower alkyl group or an acyl group, and A is a hydroxymethyl group or an esterified or amidated carboxyl group; or its pharmaceutically acceptable salt and a pharmaceutically acceptable carrier, diluent or excipient.

11 Claims, No Drawings

INDOLE DERIVATIVES, THEIR PRODUCTION AND USE

This application is a continuation of U.S. application Ser. No. 07/674,214, filed Mar. 25, 1991, now abandoned.

BACKGROUND OF THE INVENTION

1. Field of the Invention

The present invention relates to an inhibitor for bone resorption comprising indole derivatives as an active ingredient, said indole derivatives having activity for inhibiting bone resorption which is useful for treating osteoporosis.

2. Description of the Prior Arts

Osteoporosis is a morbidity or disease of bone showing symptom when bone reduction is more than some degree. The main symptoms are kyphosis or fractures of the dorsolumbar bone, body of vertebra, neck of femur, distal extremity of radius, rib, proximal extremity of humerus or the like. Various causes of osteoporosis are given, such as endocrinopathy or nutritional disorder. Conventional therapeutic agents for osteoporosis are estrogen, calcitonin, vitamin D and calcium.

The above-mentioned therapeutic agents, however, exhibit insufficient effect, since said agents are limited as to subjects suitable for treatment and are uncertain in effect.

Somo indole derivatives have been disclosed in Chem. Pharm. Bull., 19(2), pp.263-272 (1971); J. Org. Chem., Vol.37, No. 24, pp.3755-3770 (1972); J. Org. Chem., Vol. 38, No. 18, pp.3077-3084 (1973) and U.S. Pat. No. 4,014,883. However, their activities for inhibiting bone resorption are not known.

SUMMARY OF THE INVENTION

As a result of earnest studies for developing more general agents directly acting on bone to inhibit bone resorption, the inventors of this invention have discovered that indole derivatives of the formula (I) possess excellent activity for inhibiting bone resorption This invention relates to (1) an inhibitor for bone resorption comprising an indole derivative represented by the following formula (I):

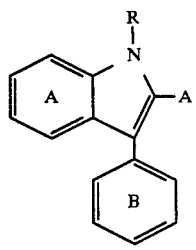

wherein each ring of A and B is optionally substituted, R is a hydrogen atom, a lower alkyl group or an acyl group, and A is a hydroxymethyl group or an esterified or amidated carboxyl group;

(2) an indole derivative represented by the following formula (I'):

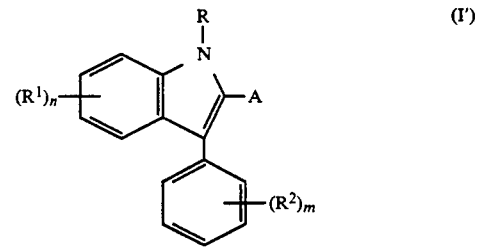

wherein $R^1$ and $R^2$ each is, the same or different, an optionally substituted hydroxyl group or an optionally substituted alkyl group, or two of each of $R^1$ and $R^2$ may be a bivalent hydrocarbon residue or alkelenedioxy group to form a ring together with the ring to which they are attached, R is a hydrogen atom, a lower alkyl group or an acyl group, A is a hydroxymethyl group or an esterified or amidated carboxylic group and n and m each is an integer of two to four.

PREFERRED EMBODIMENT OF THE INVENTION

In the formula (I), when the ring A and/or ring B is substituted, examples of the substituents may be a halogen atom, an optionally substituted alkyl, aryl or alkenyl group or an optionally substituted hydroxyl group. The number of the substituents is one to four.

Examples of the halogen atoms are fluorine, chlorine, bromine or iodine, among which fluorine or chlorine is preferable.

The alkyl group in the optionally substituted alkyl group may be any one of straight-chain, branched-chain or cyclic alkyl group having one to ten carbon atoms such as methyl, ethyl, n-propyl, isopropyl, n-butyl, isobutyl, sec-butyl, tert-butyl, n-pentyl, isopentyl, neopentyl, hexyl, heptyl, octyl, nonyl, decyl, cyclopropyl, cyclobutyl, cyclopentyl, cyclohexyl or cycloheptyl, among which those having one to six carbon atoms are preferable.

Said alkyl group may have substituent(s) such as a halogen, nitro, amino (which may be substituted by an acyl, alkyl, iminomethyl, imino(aryl-substituted) methyl, amidino and/or amino), phosphoryl, alkoxyphosphoryl, sulfo, cyano, hydroxy, carboxy, hydrazino, imino, amidino, carbamoyl, aryl (which may be substituted by a halogen, alkyl, alkoxy, alkylamino, amino, carbamoyl, sulfo, alkylsulfonyl, cyano, hydroxy, carboxy, nitro, acyloxy, aralkyloxy, phosphoryl, alkoxyphosphoryl and/or sulfoxy), heterocycle (which may be substituted by nitro, oxo, aryl, alkenylene, halogenoalkyl, alkylsulfonyl, alkyl, alkoxy, alkylamino, amino, halogen, carbamoyl, hydroxy, cyano, carboxy, phosphoryl, alkoxyphosphoryl and/or sulfo) and the like.

The aryl group in the substituted or unsubstituted aryl group may be phenyl, naphthyl, biphenyl, anthryl, indenyl or the like.

The aryl group may have substituent(s) such as a halogen, nitro, cyano, amino (which may be substituted by an alkyl, alkenyl, cycloalkyl and/or aryl), phosphoryl, sulfo, hydroxy, sulfoxy, sulfamoyl, alkyl (which may be substituted by an amino, halogen, hydroxy, cyano and/or alkoxyphosphoryl), alkoxy, aralkyloxy, alkylsulfonamido, methylenedioxy, alkoxyphosphoryl, alkylsulfonyl, alkylsulphonylamino and the like. The aryl group may form a condensed ring together with a cycloalkyl (e.g., tetrahydronaphthyl, indanyl or acenaphthenyl).

The alkenyl group in the optionally substituted alkenyl group may be any straight-chain, branched-chain or cyclic group having two to ten carbon atoms, such as allyl, vinyl, crotyl, 2-penten-1-yl, 3-penten-1-yl, 2-hexen-1-yl, 3-hexen-1-yl, 2-cyclohexenyl, 2-cyclopentenyl, 2-methyl-2-propen-1-yl, 3-methyl-2-buten-1-yl or the like, among which these groups having two to six carbon atoms are preferable.

The alkenyl group may have substituent(s) such as an alkyl having one to six carbon atoms (said alkyl may have the same substituent(s) as those on the above-mentioned alkyl groups), halogen, nitro, amino(which may be substituted by an acyl, iminomethyl, amidino, alkyl and/or aryl), phosphoryl, sulfo, cyano, hydroxy, carboxy, alkyloxycarbonyl, carbamoyl, alkylthio, arylthio, alkylsulfinyl, arylsulfinyl, alkoxyphosphoryl, alkylsulfonyl, arylsulfonyl, sulfamoyl, aryl, acyl or the like. The above-mentioned alkenyl group or alkenylene group includes its isomers (E or Z form) with respect to the double bond.

Examples of the halogen atoms as the above-mentioned substituents are chlorine, bromine, fluorine or iodine.

Suitably, the alkyl groups as the substituent are those having one to ten carbon atoms, preferably having one to six carbon atoms, more preferably having one to four carbon atoms. Examples of those alkyl groups are methyl, ethyl, n-propyl, isopropyl, n-butyl, isobutyl, tert-butyl, sec-butyl, n-pentyl, isopentyl, n-hexyl, isohexyl, heptyl, octyl, nonyl, decyl or the like.

Preferably, the cycloalkyl groups as the above-mentioned substituent are those having three to six carbon atoms, such as cyclopropyl, cyclobutyl, cyclopentyl, cyclohexyl or the like.

Preferably, the alkoxy groups as the above-mentioned substituent are those having one to four carbon atoms, such as methoxy, ethoxy, n-propoxy, isopropoxy, n-butoxy, sec-butoxy, tert-butoxy or the like.

Preferably, the aryl groups as the above-mentioned substituent are phenyl, naphthyl and the like.

Preferably, the heterocyclic groups as the above-mentioned substituent are pyridine, pyridazine, thiazole, oxazole, morpholine or the like.

Suitably, the acyl groups as the above-mentioned substituent are those having one to six carbon atoms, more preferably one to four carbon atoms, such as formyl, acetyl, propionyl, butyryl, isobutyryl, valeryl, isovaleryl, pivaloyl, hexanoyl or the like.

Preferably, the aralkyl groups as the above-mentioned substituent are benzyl, phenethyl, phenylpropyl and the like.

Preferable alkenyl or alkenylene groups as the above-mentioned substituents are methylene or the same ones as on the aforesaid alkenyl groups.

Examples of the substituted alkyl groups are trifluoromethyl, 2,2,2-trifluoroethyl, difluoromethyl, trichloromethyl, hydroxymethyl, 1- or 2-hydroxyethyl, 1- or 2-methoxyethyl, 1- or 2-ethoxyethyl, 2,2-dimethoxyethyl, 2,2-diethoxyethyl, 2-diethoxyphosphorylethyl or the like.

Examples of the substituted aryl groups include 4-chlorophenyl, 4-fluorophenyl, 2,4-dichlorophenyl, p-tolyl, 4-methoxyphenyl, 4-(N,N-dimethylamino)phenyl, 4-diethoxyphosphorylphenyl or the like.

Examples of the substituted alkenyl groups are 2,2-dichlorovinyl, 3-hydroxy-2-propen-1-yl, 2-methoxyvinyl and the like.

Examples of the optionally substituted hydroxyl groups are hydroxyl, or hydroxyl having an appropriate substituent, especially a protecting group for hydroxyl, such as an alkoxy, alkenyloxy, aralkyloxy, acyloxy or aryloxy. Preferably, said alkoxy groups are those having one to ten carbon atoms such as methoxy, ethoxy, n-propoxy, isopropoxy, n-butoxy, isobutoxy, sec-butoxy, tert-butoxy, n-pentoxy, isopentoxy, neopentoxy, hexyloxy, heptyloxy, nonyloxy, cyclobutoxy, cyclopentoxy or cyclohexyloxy). Preferably, said alkenyloxy groups are those having one to ten carbon atoms such as allyloxy, crotyloxy, 2-pentenyloxy, 3-hexenyloxy, 2-cyclopentenylmethoxy, 2-cyclohexenylmethoxy or the like. Preferably, said aralkyloxy groups are phenyl-$C_{1-4}$ alkyloxy (e.g., benzyloxy or phenethyloxy). Preferably, said acyloxy groups are alkanoyloxy (e.g., acetyloxy, propionyloxy, n-butyryloxy or isobutyryloxy) or the like. Examples of said aryloxy groups are phenoxy, 4-chlorophenoxy or the like.

Each of the alkyl, alkenyl, acyl and aryl groups in the alkyloxy, alkenyloxy, aralkyloxy, acyloxy and aryloxy groups may have substituent(s) such as a halogen (e.g., fluorine, chlorine, bromine or iodine), hydroxyl, alkoxy having one to six carbon atoms (e.g., methoxy, ethoxy, n-propoxy, isopropoxy, n-butoxy, n-pentyloxy or n-hexyloxy) or the like. The number of the substituents is preferably one to three.

Examples of said alkyloxy, alkenyloxy, aralkyloxy, acyloxy and aryloxy groups having substituent(s) are trifluoromethoxy, 2,2,2-trifluoroethoxy, difluoromethoxy, 2-methoxyethoxy, 4-chlorobenzyloxy, 2-(3,4-dimethoxyphenyl)ethoxy or the like.

In the case where the ring A and/or ring B are substituted, their substituent is preferably the optionally substituted hydroxyl group.

When there are two or more substituents on the ring A and/or ring B, these substituents may be a bivalent hydrocarbon residue or alkylenedioxy group to form a ring together with the ring A or B. For example, two substituents bond together to form a ring represented by the formula of —(CH$_2$)$_l$—, —(CH=CH)$_k$— or —O(CH$_2$)$_p$O— (in which l, k and p each represents an integer.) This ring may form a 5-, 6- or 7-membered ring together with the adjacent two carbon atoms in the ring A or B.

Examples of the lower alkyl groups represented by R in the formula (I) are straight-chain, branched-chain or cyclic groups having one to six carbon atoms, such as methyl, ethyl, n-propyl, isopropyl, n-butyl, isobutyl, sec-butyl, tert-butyl, n-pentyl, isopentyl, neopentyl, n-hexyl, cyclopropyl, cyclobutyl, cyclopentyl, cyclohexyl and the like.

Examples of the acyl groups are those produced by combining the above-mentioned alkyl groups (preferably having one to six carbon atoms) with a carbonyl group.

Preferable groups for R are hydrogen atom or lower alkyl groups having one to three carbon atoms.

Examples of the ester residues in the esterified carboxyl group represented by A in the formulas (I) and (I') are the lower alkyl groups in the explanation of R or aralkyl groups having seven to fifteen carbon atoms such as benzyl, phenethyl, phenylpropyl, benzhydryl or the like. The aralkyl group may be substituted by one to three of a halogen or alkoxy group having one to four carbon atoms.

Preferable amidated carboxyl groups are those formed by combining an amino group which may be substituted by an optionally substituted hydrocarbon residue with a carbonyl group. Examples of the optionally substituted hydrocarbon residues are optionally substituted alkyl, aryl, alkenyl or heterocyclic groups. The explanations of the optionally substituted alkyl, aryl and alkenyl groups are the same as those for the ring A and/or ring B in the formula (I).

Examples of the optionally substituted heterocyclic groups are 5–7 membered heterocyclic groups having one sulfur, nitrogen or oxygen atom, 5–6 membered heterocyclic groups having two to four nitrogen atoms or 5–6 membered heterocyclic groups having one or two nitrogen atoms and one sulfur or oxygen atom. These heterocyclic groups may be condensed with a 6-membered ring having two or less nitrogen atoms, a 5-membered ring having one sulfur atom or a benzene ring.

Examples of the heterocyclic groups are 2-pyridyl, 3-pyridyl, 4-pyridyl, pyrimidyl, pyrazinyl, pyridazinyl, pyrazolyl, imidazolyl, thiazolyl, isothiazolyl, oxazolyl, isoxazolyl, pyrido[2,3-d] pyrimidyl, benzopyranyl, 1,8-naphthyridyl, 1,5-naphthyridyl, 1,6-naphthyridyl, 1,7-naphthyridyl, quinolyl, thieno[2,3-b]pyridyl, tetrazolyl, thiadiazolyl, oxadiazolyl, triazinyl, triazolyl, thienyl, pyrrolyl, pyrrolinyl, furyl, pyrrolidinyl, benzothienyl, indolyl, imidazolidinyl, piperidyl, piperidino, piperazinyl, morpholinyl, morpholino and the like.

Said heterocyclic groups may have substituent(s) such as an amino (which may be substituted by an acyl, halogen, acyl, phenyl and/or alkyl), halogen, nitro, sulfo, cyano, hydroxy, carboxy, oxo, thioxo, alkyl having one to 10 carbon atoms (which may be substituted by an aryl, halogen, amino, hydroxy, carboxy, alkoxy, alkylsulfonyl and/or dialkylamino), cycloalkyl, alkoxy (which may be substituted by a halogen and/or hydroxy), acyl having one to four carbon atoms, aryl (which may be substituted by a halogen, nitro, alkyl, alkoxy, amino, sulfo, hydroxy and/or cyano) or oxo or the like.

Examples of the substituted heterocyclic groups are 5-chloro-2-pyridyl, 3-methoxy-2-pyridyl, 5-methyl-2-benzothiazolyl, 5-methyl-4-phenyl-2-thiazolyl, 3-phenyl-5-isoxazolyl, 4-(4-chlorophenyl)-5-methyl-2-oxazolyl, 3-phenyl-1,2,4-thiadiazole-5-yl, 5-methyl-1,3,4-thiadiazole-2-yl, 5-acetylamino-2-pyrimidyl, 3-methyl-2-thienyl, 4,5-dimethyl-2-furanyl, 4-methyl-2-morpholinyl or the like.

Preferably, optionally substituted alkyl groups and hydroxyl groups represented by $R^1$ and $R^2$ in the formula (I') are the optionally substituted alkyl and optionally substituted hydroxyl groups exemplified as the substituent of the ring A and ring B in the formula (I). The explanations of each substituent for the above groups are the same as those explained in the formula (I).

When there are two or more substituents on each benzene ring in the formula (I'), two substituents on the same benzene ring may be a bivalent hydrocarbon residue or alkylenedioxy group to form a ring together with the benzene ring to which the substituents are attached. Their examples are as explained above.

The explanations of the substituents represented by R and A in the formula (I') are the same as those explained in the formula (I).

The object compounds of the present invention can be prepared, for example, by any of the following methods.

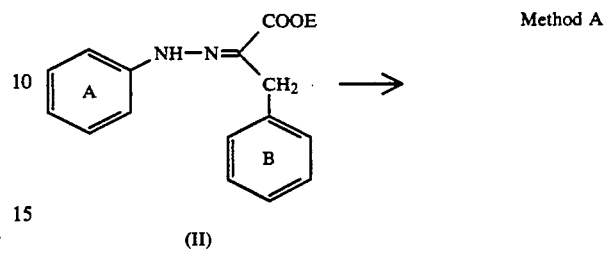

Method A (II)

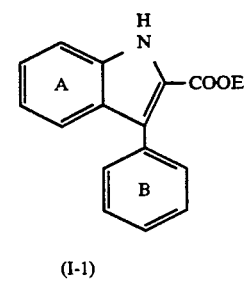

(I-1)

wherein E has the same meaning as the ester residue in the explanation of the substituent A and the ring A and ring B have the same meanings as defined above.

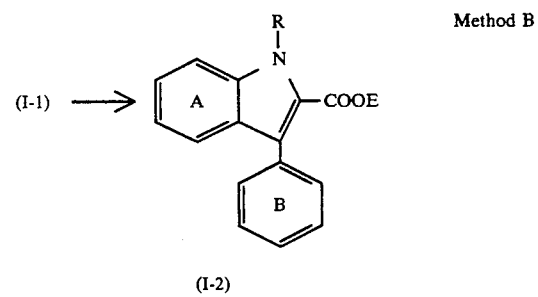

Method B (I-2)

wherein the ring A, ring B, R and E have the same meanings as defined above.

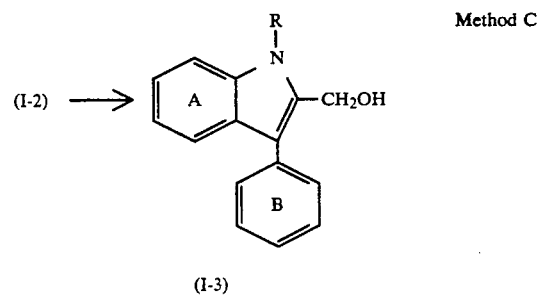

Method C (I-3)

wherein the ring A, ring B and R have the sam meanings as defined above.

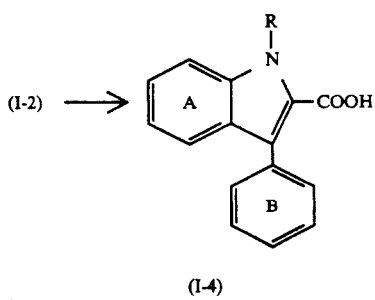

(I-2) → (I-4)

wherein the ring A, ring B and R have the same meanings as defined above.

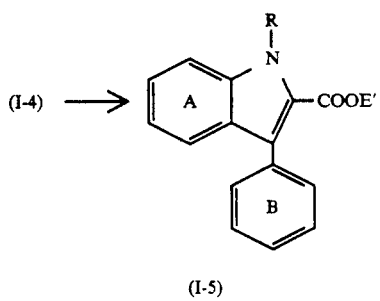

(I-4) → (I-5)

wherein E' has the same meanings as the ester residues in the explanation of the substituents represented by A and a ring A, ring B and R have the same meanings as defined above.

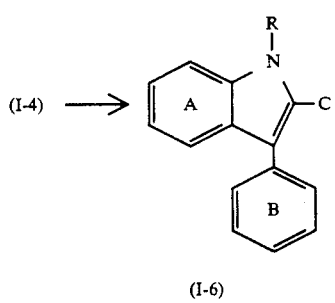

(I-4) → (I-6)

wherein C has the same meaning as the amidated carboxyl group in the explanation of the substituent A and the ring A, ring B and R have the same meanings as defined above.

Method G

When the ring A and/or ring B are substituted with a substituted hydroxyl group in the compound (I), a phenol derivative can be prepared by eliminating said substituent of hydroxyl group.

Method H

When the ring A and/or ring B are substituted with a hydroxyl group in the compound (I), a hydroxyl group substituted by alkyl, aralkyl or acyl can be prepared from the above phenolic derivative.

Each method will be explained hereinbelow.

Method A

The compound (I-1) can be prepared by heating the compound (II) in an appropriate solvent or without any solvent in the presence of an appropriate acid.

The cyclization from the compound (II) to the compound (I-1) in this method can be carried out by the same manner as the conventional Fisher Indole Synthesis. The synthesis is conducted by any known method, for example, W. Sumpter, F. Miller, The Chemistry of Heterocyclic Compounds, 8, Heterocyclic Compounds with Indole and Carbazole Systems [Interscience Publishers, Inc. New York, (1954)]; W. Houlihan, 25, pp.232 [Wiley-Interscience, (1972)]; Shinjikken Kagakukoza 14, Synthesis and Reaction of Organic Compound (IV) [Chemical Society of Japan, Maruzen, (1978)]; and Daiyukikagaku 14, Heterocyclic Compounds 1, pp.342 [Asakura Shoten, (1959)]. For example, the synthesis is carried out in a solvent such as an alcohol (e.g., ethanol, methanol, propanol, isopropanol or the like) in the presence of hydrochloric acid, sulfuric acid, acetic acid, formic acid, phosphoric anhydride or Lewis acid (e.g., zinc chloride). The acid is used preferably in an amount of from about 0.5 to 10 mols to one mol of the compound (II). The reaction temperature is usually from about 10° C. to 200° C., preferably from about 30° C. to 150° C. The reaction time is about 0.5 to 100 hours, preferably about 1 to 30 hours. Acetic acid can be used as a solvent when it is used as an acid catalyst. The compound (II), which is the starting material in this method, can be prepared by known Japp-Klingemann reaction disclosed in The Chemistry of Heterocyclic Compounds, 8, Heterocyclic Compounds with Indole and Carbazole Systems by W. Sumpter, F. Miller [Interscience Publishers, Inc., New York (1954)].

Method B

The compound (I-2) can be prepared by reacting the compound (I-1) with a compound represented by the formula R-X [in which X is a leaving group such as a halogen (e.g., chlorine, bromine or iodine) or sulfonyloxy (e.g., mesyloxy, tosyloxy or benzenesulfonyloxy) and R has the same meaning as defined above] in the presence of a base (e.g., sodium hydride, potassium hydride, sodium amide, triethylamine, N-methylmorpholine, sodium hydrogencarbonate, potassium hydrogencarbonate, sodium carbonate, potassium carbonate or the like). This reaction is carried out in a suitable solvent such as tetrahydrofuran, dioxane, ether, toluene, xylene, benzene, 1,2-dichloroethane, 1,1,2,2-tetrachloroethane, N,N-dimethylformamide, dimethylsulfoxide or the like) at a temperature of about −20° C. to 100° C., preferably about −10° C. to 50° C. The compound (R-X) is preferably used in an excess amount to the compound (I-1).

Method C

This reaction can be conducted by a known reduction method, for example, a method disclosed in Shinjikken Kagakukoza 15, Oxidation and Reduction [II] (Maruzen, 1977), a reduction with a metal and a metal salt, reduction with a metal hydride compound, reduction with a metal hydride complex, reduction by a hydrogen transfer reaction or reduction by a catalytic hydrogenation and so on.

Method D

The compound (I-4) can be prepared by hydrolyzing the compounds (I-1) or (I-2) prepared in Method A or Method B. The hydrolysis can be carried out by a known method in a solvent in the presence of an acid such as hydrochloric acid, sulfuric acid, acetic acid, hydrobromic acid or the like or a base such as potassium carbonate, sodium carbonate, sodium methoxide, sodium ethoxide, potassium tert-butoxide, sodium hydroxide, potassium hydroxide, lithium hydroxide or the like. Suitable solvents to be used are mixtures of water and organic solvents such as alcohols (e.g., methanol or ethanol), ether (e.g., tetrahydrofuran or dioxane), N,N-dimethylformamide, dimethylsulfoxide, acetone and the like. The acid or base is preferably used in an excess amount (base: 1.2 to 6 equivalents; acid: 2 to 50 equivalents) to the compound (I-1) or (I-2). The reaction is carried out at about −20° C. to 150° C., preferably about −10° C. to 100° C.

Method E

The compound (I-5) can be prepared by esterifying the carboxylic acid derivative (I-4). This esterification can be conducted by any known method, for example, a method for directly reacting the compound (I-4) with an alkyl halide in the presence of a base or a method for reacting an alcohol with a reactive derivative of the compound (I-4) such as acid anhydride, acid halide (e.g., acid chloride or acid bromide), imidazolide or mixed anhydride (e.g., anhydride with methyl carbonate, anhydride with ethyl carbonate, anhydride with isobutyl carbonate or the like).

Method F

The compound (I-6) can be prepared by amidating the carboxylic acid derivative (I-4). This reaction can be conducted by any known method, for example, a method for directly condensing the compound (I-4) and an amine derivative in the presence of dicyclohexyl carbodiimide or the like or a method for reacting an amine derivative with a reactive derivative of the compound (I-4), such as acid anhydride, acid halide (e.g., acid chloride or acid bromide), imidazolide or mixed anhydride (e.g., anhydride with methyl carbonate, anhydride with ethyl carbonate, anhydride with isobutyl carbonate or the like). The most convenient method is the one using the acid halide or mixed anhydride of the compound (I-4). In the case of using the acid halide, the reaction is carried out in a solvent (e.g., chloroform, dichloromethane, ethyl acetate, tetrahydrofuran, water or mixture thereof) in the presence of a base (e.g., triethylamine, N-methylmorpholine, sodium hydrogencarbonate, potassium hydrogencarbonate, sodium carbonate or potassium carbonate) at about −10° C. to 50° C. The amine derivative is used in an amount of about 1 to 1.2 mols to the compound (I-4). In the case of using the mixed anhydride, the compound (I-4) is preferably reacted with a chlorocarbonic ester (e.g., methyl chlorocarbonate, ethyl chlorocarbonate or isobutyl chlorocarbonate) in the presence of a base (e.g., triethylamine, N-methylmorpholine, sodium hydrogencarbonate, potassium hydrogencarbonate, sodium carbonate or potassium carbonate) in a suitable solvent (e.g., chloroform, dichloromethane, ethyl acetate, tetrahydrofuran, water or mixture thereof) at about −10° C. to 30° C. The amount of the amine derivative to be used is about 1 to 1.2 mols to the compound (I-4).

Method G

The compound (I) in which the ring A and/or B have a substituted hydroxyl group can eliminate its substituent of hydroxyl group to afford a phenol derivative. The conversion of the alkyloxy or aralkyloxy derivative to the phenol derivative can be preferably conducted by use of boron tribromide or boron trichloride. This reaction is carried out in an inert solvent such as carbon tetrachloride, chloroform, dichloromethane, 1,2-dichloroethane, 1,1,2,2-tetrachloroethane or the like at about −50° C. to 40° C., preferably about −20° C. to 30° C. Boron tribromide or boron trichloride is used in an excess amount to the compound (I). The conversion of the acyloxy derivatives to the phenol derivatives is conducted by the same manner as in Method D.

Method H

The hydroxyl group substituted by an alkyl, aralkyl or acyl can be prepared from the compound (I) in which the substituent on the ring A and/or ring B is a hydroxyl group.

The alkylation or aralkylation of the hydroxyl group can be carried out by the same manner as in Method B or analogous ones thereto. The acylation can be conducted by any known methods. Generally, the acylation is carried out by reacting, in an anhydrous organic solvent, the compound (I) with an acylating agent which can introduce the above-mentioned acyl group, such as acid halide, acid anhydride, activated ester of carboxylic acid or the like. The reaction can be carried out in the presence of an appropriate organic or inorganic base at about 0° C. to 70° C., preferably about 20° C. to 50° C. for about 0.5 to 48 hours, preferably about 1 to 20 hours.

A pharmaceutically acceptable acid addition salt of the compound (I) can easily be prepared by reacting the compound (I) with an inorganic acid such as hydrochloric acid, sulfuric acid, hydrobromic acid or phosphoric acid or an organic acid such as maleic acid, fumaric acid, tartaric acid, citric acid, oxalic acid or benzoic acid by known methods.

Further, a pharmaceutically acceptable salt with an alkali metal such as potassium or sodium can be prepared from the compound (I) having in its molecule an acid group such as carboxylic acid.

A method for preparing the compound (I) will hereinbelow be explained with reference to Reference Examples and Examples, by which this invention shall not be limited.

REFERENCE EXAMPLE 1

A solution of sodium nitrite (0.414 g) in water (2.0 ml) was dropwise added to a solution of 3,4-xylidine (0.61 g) in concentrated hydrochloric acid (1.5 ml) at a temperature of 0° C., followed by stirring for 30 minutes at 0° C. To the mixture were added sodium acetate (1.23 g) and methyl 2-(3,4-dimethoxybenzyl)acetoacetate (1.33 g). After stirring for an hour at room temperature, the reaction mixture was poured into water and extracted with ethyl ether. The ethereal layer was washed with a saturated sodium hydrogencarbonate aqueous solution and water, dried (MgSO$_4$) and concentrated under reduced pressure. The residue was dissolved in methanol (20 ml), to which 1N-KOH methanolic solution (5 ml) was dropwise added at 0° C. After stirring for an hour at 0° C., the resultant mixture was neutralized with acetic acid and poured into water. The precipitate was collected by filtration and recrystallized from acetone-methanol to give methyl 3-(3,4-dimethoxyphenyl)-2-(3,4-dimethylphenylhydrazino)propionate (1.25 g, 70%) as pale red prisms.

mp: 148°–150° C.

Elementary Analysis for C$_{20}$H$_{24}$N$_2$O$_4$: Calc.: C, 67.40; H, 6.79; N, 7.86. Found: C, 67.62; H, 6.87; N, 7.82.

REFERENCE EXAMPLES 2-41

Compounds listed in Table 1 were obtained by the same manner as in Reference Example 1.

EXAMPLE 1

A mixture of methyl 2-(3,4-dimethoxyphenylhydrazino)-3-(3,4-dimethylphenyl)propionate (0.8 g), con-

TABLE 1

| No. of Examples | $R^1$ | $R^2$ | $R^3$ | $R^4$ | $R^5$ | $R^6$ | $R^7$ | Yield (%) | MP (°C.) | Solvent for recrystallization |
|---|---|---|---|---|---|---|---|---|---|---|
| 2 | H | $CH_3O$ | $CH_3O$ | H | $CH_3O$ | $CH_3O$ | H | 78 | 142-144 | methanol |
| 3 | H | $CH_3O$ | $CH_3O$ | H | H | $CH_3O$ | H | 64 | 101-102 | ether* |
| 4 | H | $CH_3O$ | $CH_3O$ | H | —$OCH_2O$— | | H | 73 | 97-99 | ether |
| 5 | H | $CH_3O$ | $CH_3O$ | H | H | $CH_3$ | H | 60 | 109-110 | ether |
| 6 | H | $CH_3O$ | $CH_3O$ | H | H | H | H | 66 | 107-108 | ether |
| 7 | H | $CH_3O$ | $CH_3O$ | H | $CH_3$ | $CH_3$ | H | 50 | 117-118 | methanol |
| 8 | H | $CH_3O$ | $CH_3O$ | H | Cl | Cl | H | 58 | 92-93 | isopropyl ether |
| 9 | H | $CH_3O$ | $CH_3O$ | H | H | Cl | H | 66 | 123-124 | methanol |
| 10 | H | $CH_3O$ | $CH_3O$ | $CH_3O$ | H | H | $CH_3O$ | 70 | 103-104 | isopropyl ether |
| 11 | H | $CH_3O$ | $CH_3O$ | H | $CH_3O$ | H | $CH_3O$ | 50 | 118-119 | ether |
| 12 | H | $CH_3O$ | $CH_3O$ | H | $C_2H_5O$ | $C_2H_5O$ | H | 65 | 98-99 | methanol-water |
| 13 | H | $CH_3O$ | $CH_3O$ | H | H | $C_2H_5O$ | H | 57 | 116-117 | ether |
| 14 | H | —$OCH_2O$— | | H | $CH_3O$ | $CH_3O$ | H | 58 | 174-175 | methanol |
| 15 | H | —$O(CH_2)_2O$— | | H | $CH_3O$ | $CH_3O$ | H | 76 | 181-183 | chloroform-acetone |
| 16 | H | H | $CH_3O$ | H | $CH_3O$ | $CH_3O$ | H | 76 | 144-145 | acetone-methanol |
| 17 | H | H | $CH_3$ | H | $CH_3O$ | $CH_3O$ | H | 70 | 175-177 | acetone-methanol |
| 18 | $CH_3$ | H | $CH_3$ | H | $CH_3O$ | $CH_3O$ | H | 78 | 157-158 | acetone-methanol |
| 19 | H | H | H | H | $CH_3O$ | $CH_3O$ | H | 66 | 155-157 | acetone-methanol |
| 20 | H | H | Cl | H | $CH_3O$ | $CH_3O$ | H | 30 | 204-206 | acetone-methanol |
| 21 | H | Cl | $CH_3$ | H | $CH_3O$ | $CH_3O$ | H | 21 | 149-150 | methanol |
| 22 | H | —$(CH_2)_3$— | | H | $CH_3O$ | $CH_3O$ | H | 75 | 149-150 | acetone-methanol |
| 23 | —$(CH_2)_4$— | | H | H | $CH_3O$ | $CH_3O$ | H | 46 | 158-159 | acetone-methanol |
| 24 | H | —$O(CH_2)_2O$— | | H | H | $CH_3O$ | H | 74 | 125-127 | ether |
| 25 | H | $CH_3$ | $CH_3$ | H | H | $CH_3O$ | H | 76 | 115-116 | methanol |
| 26 | H | H | $CH_3O$ | H | $CH_3$ | $CH_3$ | H | 71 | 93-94 | methanol |
| 27 | H | H | $CH_3O$ | H | H | $CH_3O$ | H | 89 | oil[1)] | — |
| 28 | H | H | $CH_3O$ | H | H | $C_2H_5O$ | H | 84 | oil[2)] | — |
| 29 | H | H | H | H | H | H | H | 58 | 88-89 | isopropyl ether |
| 30 | H | $CH_3$ | $CH_3$ | H | H | $CH_3$ | H | 70 | 99-100 | isopropyl ether |
| 31 | H | H | $CH_3$ | H | H | H | H | 97 | oil[3)] | — |
| 32 | H | H | $CH_3$ | H | $CH_3$ | $CH_3$ | H | 52 | 110-111 | methanol-water |
| 33 | H | H | $CH_3$ | H | H | Cl | H | 93 | oil[4)] | — |
| 34 | H | H | $CH_3$ | H | Cl | Cl | H | 70 | 122-123 | acetone-methanol |
| 35 | H | H | $CH_3$ | H | H | $CH_3$ | H | 57 | 89-90 | isopropyl ether |
| 36 | H | $CH_3O$ | $CH_3O$ | H | $CH_3O$ | $CH_3O$ | $CH_3O$ | 42 | 132-133 | acetone-methanol |
| 37 | H | —$O(CH_2)_2O$— | | H | $CH_3O$ | $CH_3O$ | $CH_3O$ | 37 | 137-138 | methanol-dichloromethane |
| 38 | H | —$OCH_2O$— | | H | $C_2H_5O$ | $C_2H_5O$ | H | 28 | 128-129 | ethyl acetate-hexane |
| 39 | H | —$O(CH_2)_2O$— | | $CH_3O$ | $CH_3O$ | $CH_3O$ | H | 74 | 132-133 | ethyl acetate-hexane |
| 40 | H | $CH_3O$ | $CH_3O$ | $CH_3O$ | H | $CH_3O$ | $CH_3O$ | 73 | 136-137 | ethyl acetate-hexane |
| 41 | H | —$OCH_2O$ | | $CH_3O$ | H | $CH_3O$ | $CH_3O$ | 46 | 136-137 | ethyl acetate-hexane |

Note [1)] to [4)]: crude oil
*ethyl ether centrated sulfuric acid (1 ml) and methanol (25 ml) was refluxed for 4 hours. The reaction mixture was poured into water and extracted with ethyl acetate. The ethyl acetate layer was washed with water, dried (MgSO$_4$) and concentrated. The precipitated crystals were collected by filtration and recrystallized from ethyl ether to give methyl 5,6-dimethoxy-3-(3,4-dimethylphenyl)indole-2-carboxylate (0.457 g, 60%) as colorless prisms.

mp: 185°–186° C.

Elementary Analysis for $C_{20}H_{21}NO_4$: Calc.: C, 70.78; H, 6.24; N, 4.13. Found: C, 70.83; H, 6.32; N, 4.10.

EXAMPLES 2–41

Compounds listed in Table 2 were obtained by the same manner as in Example 1.

TABLE 2

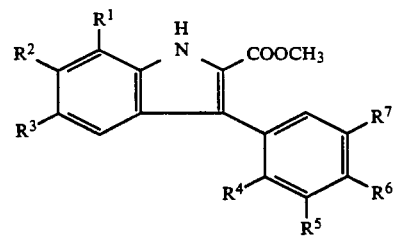

| No. of Examples | $R^1$ | $R^2$ | $R^3$ | $R^4$ | $R^5$ | $R^6$ | $R^7$ | Yield (%) | MP (°C.) | Solvent for recrystallization |
|---|---|---|---|---|---|---|---|---|---|---|
| 2 | H | CH$_3$O | CH$_3$O | H | CH$_3$O | CH$_3$O | H | 68 | 164–166 | acetone-methanol |
| 3 | H | CH$_3$O | CH$_3$O | H | H | CH$_3$O | H | 73 | 162–163 | acetone-methanol |
| 4 | H | CH$_3$O | CH$_3$O | H | —OCH$_2$O— | | H | 69 | 214–216 | acetone-methanol |
| 5 | H | CH$_3$O | CH$_3$O | H | H | CH$_3$ | H | 66 | 174–175 | ether |
| 6 | H | CH$_3$O | CH$_3$O | H | H | H | H | 69 | 151–152 | ether |
| 7 | H | CH$_3$O | CH$_3$O | H | Cl | Cl | H | 51 | 178–179 | ether |
| 8 | H | CH$_3$O | CH$_3$O | H | H | Cl | H | 58 | 193–194 | ether |
| 9 | H | CH$_3$O | CH$_3$O | CH$_3$O | H | H | CH$_3$O | 58 | 195–196 | methanol |
| 10 | H | CH$_3$O | CH$_3$O | H | CH$_3$O | H | CH$_3$O | 61 | 160–161 | methanol |
| 11 | H | CH$_3$O | CH$_3$O | H | C$_2$H$_5$O | C$_2$H$_5$O | H | 41 | 149–150 | methanol |
| 12 | H | CH$_3$O | CH$_3$O | H | H | C$_2$H$_5$O | H | 73 | 160–161 | methanol |
| 13 | H | —OCH$_2$O— | | H | CH$_3$O | CH$_3$O | H | 65 | 245–247 | acetone |
| 14 | H | —O(CH$_2$)$_2$O— | | H | CH$_3$O | CH$_3$O | H | 46 | 235–237 | acetone-methanol |
| 15 | H | CH$_3$ | CH$_3$ | H | CH$_3$O | CH$_3$O | H | 56 | 223–225 | ethyl acetate |
| 16 | H | H | CH$_3$O | H | CH$_3$O | CH$_3$O | H | 41 | 159–160 | ether |
| 17 | H | H | CH$_3$ | H | CH$_3$O | CH$_3$O | H | 46 | 158–160 | ether |
| 18 | CH$_3$ | H | CH$_3$ | H | CH$_3$O | CH$_3$O | H | 35 | 174–175 | ether |
| 19 | H | H | H | H | CH$_3$O | CH$_3$O | H | 30 | 179–180 | ether |
| 20 | H | H | Cl | H | CH$_3$O | CH$_3$O | H | 7 | 150–151 | ether-hexane |
| 21 | H | Cl | CH$_3$ | H | CH$_3$O | CH$_3$O | H | 16 | 212–213 | ether |
| 22 | H | —(CH$_2$)$_3$— | | H | CH$_3$O | CH$_3$O | H | 46 | 185–186 | methanol |
| 23 | —(CH$_2$)$_4$— | | H | H | CH$_3$O | CH$_3$O | H | 55 | 225–227 | acetone |
| 24 | H | —O(CH$_2$)$_2$O— | | H | H | CH$_3$O | H | 58 | 200–202 | acetone-methanol |
| 25 | H | CH$_3$ | CH$_3$ | H | H | CH$_3$O | H | 56 | 214–215 | ethyl acetate |
| 26 | H | H | CH$_3$O | H | CH$_3$ | CH$_3$ | H | 51 | 181–182 | ether |
| 27 | H | H | CH$_3$O | H | H | CH$_3$O | H | 28[1] | 152–153 | ether |
| 28 | H | H | CH$_3$O | H | H | C$_2$H$_5$O | H | 12[2] | 161–162 | isopropyl ether |
| 29 | H | H | H | H | H | H | H | 79 | 138–139 | methanol |
| 30 | H | CH$_3$ | CH$_3$ | H | H | CH$_3$ | H | 65 | 203–204 | acetone-methanol |
| 31 | H | H | CH$_3$ | H | H | H | H | 59[3] | 171–172 | acetone-methanol |
| 32 | H | H | CH$_3$ | H | CH$_3$ | CH$_3$ | H | 81 | 163–164 | methanol |
| 33 | H | H | CH$_3$ | H | H | Cl | H | 58[4] | 188–189 | acetone-methanol |
| 34 | H | H | CH$_3$ | H | Cl | Cl | H | 64 | 172–173 | acetone-methanol |
| 35 | H | H | CH$_3$ | H | H | CH$_3$ | H | 82 | 167–168 | methanol |
| 36 | H | CH$_3$O | CH$_3$O | H | CH$_3$O | CH$_3$O | CH$_3$O | 24 | 179–180 | methanol |
| 37 | H | —O(CH$_2$)$_2$O— | | H | CH$_3$O | CH$_3$O | CH$_3$O | 74 | 204–205 | methanol-chloroform |
| 38 | H | —OCH$_2$O— | | H | C$_2$H$_5$O | C$_2$H$_5$O | H | 44 | 208–209 | ethyl acetate-hexane |
| 39 | H | —O(CH$_2$)$_2$O— | | CH$_3$O | H | CH$_3$O | CH$_3$O | 34 | 190–191 | ethyl acetate-hexane |
| 40 | H | CH$_3$O | CH$_3$O | CH$_3$O | H | CH$_3$O | CH$_3$O | 34 | 104–105 | ethyl acetate-hexane |
| 41 | H | —OCH$_2$O— | | CH$_3$O | H | CH$_3$O | CH$_3$O | 30 | 218–219 | ethyl acetate- |

TABLE 2-continued

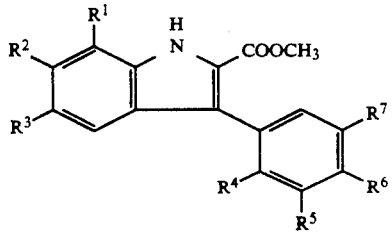

| No. of Examples | R¹ | R² | R³ | R⁴ | R⁵ | R⁶ | R⁷ | Yield (%) | MP (°C.) | Solvent for recrystallization |
|---|---|---|---|---|---|---|---|---|---|---|
| | | | | | | | | | | hexane |

[1] Yield from Reference Example 27
[2] Yield from Reference Example 28
[3] Yield from Reference Example 31
[4] Yield from Reference Example 33

EXAMPLE 42

To a solution of methyl 5,6-dimethoxy-3-(3,4-dimethoxyphenyl)indole-2-carboxylate (7.5 g) in N,N-dimethylformamide (100 ml) was added oily sodium hydride (60%, 1.6 g) and the mixture was stirred for 30 minutes at room temperature. After dropwise addition of ethyl iodide (4.8 ml), the reaction mixture was further stirred for 2 hours at room temperature, poured into water and extracted with ethyl acetate. The ethyl acetate layer was washed with water, dried (MgSO₄) and concentrated. The precipitated crystals were collected by filtration and recrystallized from ethyl ether to give methyl 1-ethyl-5,6-dimethoxy-3-(3,4-dimethoxyphenyl)indole-2-carboxylate (6.38 g, 77%) as pale red prisms. mp: 191°–192° C.

Elementary Analysis for $C_{22}H_{25}NO_6$: Calc.: C, 66.15; H, 6.31; N, 3.51. Found: C, 66.14; H, 6.43; N, 3.35.

EXAMPLES 43–75

Compounds listed in Table 3 were obtained by the same manner as in Example 42.

TABLE 3

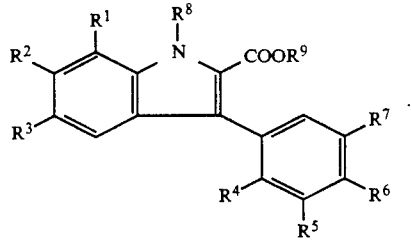

| No. of Examples | R¹ | R² | R³ | R⁴ | R⁵ | R⁶ | R⁷ | R⁸ | R⁹ | Yield (%) | MP (°C.) | Solvent for recrystallization |
|---|---|---|---|---|---|---|---|---|---|---|---|---|
| 43 | H | CH₃O | CH₃O | H | CH₃O | CH₃O | H | CH₃ | CH₃ | 93 | 206–208 | acetone |
| 44 | H | CH₃O | CH₃O | H | CH₃O | CH₃O | H | n-C₃H₇ | CH₃ | 74 | 131–132 | ether |
| 45 | H | CH₃O | CH₃O | H | CH₃O | CH₃O | H | (CH₃)₂CH | CH₃ | 90 | 147–149 | methanol |
| 46 | H | CH₃O | CH₃O | H | CH₃O | CH₃O | H | n-C₄H₉ | CH₃ | 74 | 118–119 | ether |
| 47 | H | CH₃O | CH₃O | H | CH₃O | CH₃O | H | n-C₅H₁₁ | CH₃ | 73 | 116–117 | ether |
| 48 | H | CH₃O | CH₃O | H | CH₃O | CH₃O | H | COOC₂H₅ | CH₃ | 82 | 148–150 | acetone |
| 49 | H | CH₃O | CH₃O | H | CH₃O | CH₃O | H | CH₂COOC₂H₅ | CH₃ | 91 | 197–199 | ethyl acetate |
| 50 | H | CH₃O | CH₃O | H | CH₃O | CH₃O | H | COOCH₂Ph | CH₃ | 84 | 121–122 | ether |
| 51 | H | CH₃O | CH₃O | H | CH₃O | CH₃O | H | COCH₃ | CH₃ | 64 | 158–159 | acetone |
| 52 | H | CH₃O | CH₃O | H | CH₃O | CH₃O | H | COC₂H₅ | CH₃ | 49 | 158–160 | ether |
| 53 | H | CH₃O | CH₃O | H | CH₃O | CH₃O | H | COCH=CHCH₃ | CH₃ | 12 | 152–154 | ether |
| 54 | H | CH₃O | CH₃O | H | CH₃O | CH₃O | H | C₂H₅ | (CH₃)₃C | 87 | 128–129 | ether |
| 55 | H | —O(CH₂)₂O— | | H | CH₃O | CH₃O | H | C₂H₅ | CH₃ | 88 | 224–225 | chloroform-methanol |
| 56 | H | —OCH₂O— | | H | CH₃O | CH₃O | H | C₂H₅ | CH₃ | 77 | 203–204 | chloroform-acetone |
| 57 | H | CH₃O | CH₃O | H | CH₃O | CH₃O | CH₃O | C₂H₅ | CH₃ | 67 | 142–143 | methanol |
| 58 | H | —O(CH₂)₂O— | | H | CH₃O | CH₃O | CH₃O | CH₃ | CH₃ | 32 | 160–161 | methanol-dichloromethane |
| 59 | H | —O(CH₂)₂O— | | H | CH₃O | CH₃O | CH₃O | C₂H₅ | CH₃ | 60 | 161–162 | methanol-dichloromethane |
| 60 | H | —O(CH₂)₂O— | | H | CH₃O | CH₃O | CH₃O | (CH₃)₂CH | CH₃ | 18 | 190–191 | methanol-dichloromethane |
| 61 | H | —O(CH₂)₂O— | | H | C₂H₅O | C₂H₅O | H | CH₃ | CH₃ | 81 | 174–175 | ethyl acetate-hexane |
| 62 | H | —O(CH₂)₂O— | | H | C₂H₅O | C₂H₅O | H | C₂H₅ | CH₃ | 60 | 181–182 | ethyl acetate-hexane |
| 63 | H | —O(CH₂)₂O— | | H | C₂H₅O | C₂H₅O | H | (CH₃)₂CH | CH₃ | 53 | 155–156 | ethyl acetate- |

TABLE 3-continued

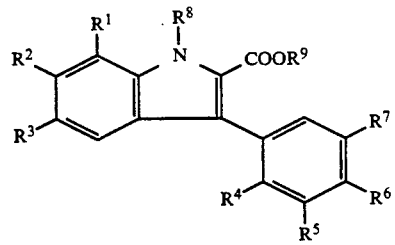

| No. of Examples | $R^1$ | $R^2$ | $R^3$ | $R^4$ | $R^5$ | $R^6$ | $R^7$ | $R^8$ | $R^9$ | Yield (%) | MP (°C.) | Solvent for recrystallization |
|---|---|---|---|---|---|---|---|---|---|---|---|---|
| 64 | H | —OCH$_2$O— | | H | C$_2$H$_5$O | C$_2$H$_5$O | H | CH$_3$ | CH$_3$ | 89 | 156-157 | ethyl acetate-hexane |
| 65 | H | —OCH$_2$O— | | H | C$_2$H$_5$O | C$_2$H$_5$O | H | C$_2$H$_5$ | CH$_3$ | 90 | 178-179 | ethyl acetate-hexane |
| 66 | H | —OCH$_2$O— | | H | C$_2$H$_5$O | C$_2$H$_5$O | H | (CH$_3$)$_2$CH | CH$_3$ | 11 | 144-145 | ethyl acetate-hexane |
| 67 | H | —O(CH$_2$)$_2$O— | | CH$_3$O | H | CH$_3$O | CH$_3$O | CH$_3$ | CH$_3$ | 73 | 187-188 | ethyl acetate-hexane |
| 68 | H | —O(CH$_2$)$_2$O— | | CH$_3$O | H | CH$_3$O | CH$_3$O | C$_2$H$_5$ | CH$_3$ | 59 | 191-192 | ethyl acetate-hexane |
| 69 | H | —O(CH$_2$)$_2$O— | | CH$_3$O | H | CH$_3$O | CH$_3$O | (CH$_3$)$_2$CH | CH$_3$ | 13 | 178-179 | ethyl acetate-hexane |
| 70 | H | CH$_3$O | CH$_3$O | CH$_3$O | H | CH$_3$O | CH$_3$O | CH$_3$ | CH$_3$ | 60 | 158-159 | ethyl acetate-hexane |
| 71 | H | CH$_3$O | CH$_3$O | CH$_3$O | H | CH$_3$O | CH$_3$O | C$_2$H$_5$ | CH$_3$ | 60 | 135-136 | ethyl acetate-hexane |
| 72 | H | CH$_3$O | CH$_3$O | CH$_3$O | H | CH$_3$O | CH$_3$O | (CH$_3$)$_2$CH | CH$_3$ | 33 | 157-158 | ethyl acetate-hexane |
| 73 | H | —OCH$_2$O— | | CH$_3$O | H | CH$_3$O | CH$_3$O | CH$_3$ | CH$_3$ | 92 | 192-193 | ethyl acetate-hexane |
| 74 | H | —OCH$_2$O— | | CH$_3$O | H | CH$_3$O | CH$_3$O | C$_2$H$_5$ | CH$_3$ | 84 | 153-154 | ethyl acetate-hexane |
| 75 | H | —OCH$_2$O— | | CH$_3$O | H | CH$_3$O | CH$_3$O | (CH$_3$)$_2$CH | CH$_3$ | 42 | 179-180 | ethyl acetate-hexane |

EXAMPLE 76

A solution of methyl 5,6-dimethoxy-3-(4-methoxyphenyl)indole-2-carboxylate (0.25 g) in tetrahydrofuran (10 ml) was dropwise added to a suspension of lithium aluminum hydride (LiAlH$_4$) (56 mg) in tetrahydrofuran (10 ml) at room temperature, followed by stirring for 2 hours at room temperature. After adding water, the mixture was extracted with ethyl acetate. The ethyl acetate layer was washed with water, dried (MgSO$_4$) and concentrated. The precipitated crystals were collected by filtration and recrystallized from acetone to give 2-hydroxymethyl-5,6-dimethoxy-3-(4-methoxyphenyl)-indole (0.145 g, 63%) as colorless prisms. mp: 169°-170° C.

Elementary Analysis for C$_{18}$H$_{19}$NO$_4$: Calc.: C, 68.99; H, 6.11; N, 4.47. Found: C, 68.93; H, 6.21; N, 4.39.

EXAMPLES 77-80

Compounds listed in Table 4 were obtained by the same manner as in Example 76.

TABLE 4

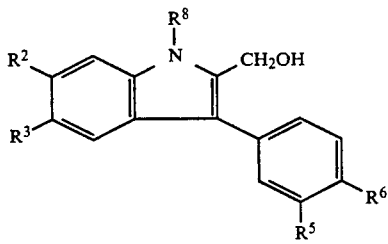

| No. of Examples | $R^2$ | $R^3$ | $R^5$ | $R^6$ | $R^8$ | Yield (%) | MP (°C.) | Solvent for recrystallization |
|---|---|---|---|---|---|---|---|---|
| 77 | CH$_3$O | CH$_3$O | CH$_3$O | CH$_3$O | H | 69 | 165-167 | ether |
| 78 | —O(CH$_2$)$_2$O— | | CH$_3$O | CH$_3$O | H | 68 | 201-202 | acetone-isopropylether |
| 79 | CH$_3$O | CH$_3$O | CH$_3$O | CH$_3$O | C$_2$H$_5$ | 83 | 182-183 | acetone |
| 80 | CH$_3$O | CH$_3$O | CH$_3$O | CH$_3$O | (CH$_3$)$_2$CH | 70 | 140-141 | ether |

EXAMPLE 81

A mixture of methyl 5,6-dimethoxy-3-(3,4-dimethoxyphenyl)indole-2-carboxylate (0.54 g), 2N-NaOH (10 ml) and methanol (25 ml) was refluxed for 3 hours under stirring. The reaction mixture was poured into water, acidified with 6N-HCl and extracted with chloroform. The chloroform layer was washed with water, dried (MgSO$_4$) and concentrated. The precipitated crystals were collected by filtration and recrystallized from methanol to give 5,6-dimethoxy-3-(3,4-dimethoxyphenyl)indole-2-carboxylic acid (0.443 g, 85%) as pale red prisms.

mp: 198°–200° C. Elementary Analysis for C$_{18}$H$_{19}$NO$_6$: Calc.: C, 63.86; H, 5.36; N, 3.92. Found: C, 64.09; H, 5.44; N, 3.85.

EXAMPLES 82–85

Compounds listed in Table 5 were obtained by the same manner as in Example 81.

TABLE 5

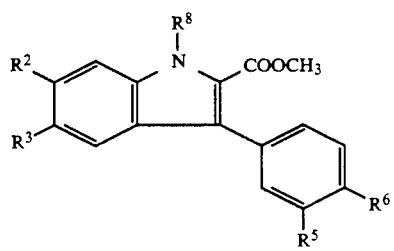

| No. of Examples | R$^2$ | R$^3$ | R$^5$ | R$^6$ | R$^8$ | Yield (%) | MP (°C.) | Solvent for recrystallization |
|---|---|---|---|---|---|---|---|---|
| 82 | CH$_3$O | CH$_3$O | H | CH$_3$O | H | 94 | 198–200 | ether-isopropyl ether |
| 83 | CH$_3$O | CH$_3$O | —OCH$_2$O— | | H | 87 | 227–229 | acetone-methanol |
| 84 | —O(CH$_2$)$_2$O— | | CH$_3$O | CH$_3$O | H | 85 | 235–236 | acetone-methanol |
| 85 | CH$_3$O | CH$_3$O | CH$_3$O | CH$_3$O | C$_2$H$_5$ | 91 | 189–190 | acetone |

EXAMPLE 86

Oxalyl chloride (0.1 ml) was added to a solution of 5,6-dimethoxy-3-(3,4-dimethoxyphenyl)indole-2-carboxylic acid (0.357 g) and N,N-dimethylformamide (1 drop) in tetrahydrofuran (10 ml) and stirred for 30 minutes at room temperature. The resultant was concentrated under reduced pressure. The residue was dissolved in tetrahydrofuran (5 ml). On the other hand, oily sodium hydride (60%, 0.133 g) was added to a solution of diethylaminophosphonate (0.92 g) in tetrahydrofuran (5 ml) with ice-cooling and stirred for 15 minutes at the same temperature. To the resultant mixture was added the above-mentioned tetrahydrofuran solution with ice-cooling. The reaction mixture was stirred for 30 minutes with ice-cooling, poured into water and extracted with ethyl acetate. The ethyl acetate layer was successively washed with sodium hydrogen carbonate saturated aqueous solution, 2N-HCl and water, dried (MgSO$_4$) and concentrated. The precipitated crystals were collected by filtration and recrystallized from ethyl acetate to give N-diethoxyphosphoryl-5,6-dimethoxy-3-(3,4-dimethoxyphenyl)indole-2-carboxamide (0.056 g, 11%) as pale yellow prisms.

mp: 217°–219° C.

Elementary Analysis for C$_{23}$H$_{29}$N$_2$O$_8$P.H$_2$O: Calc.: C, 54.12; H, 6.12; N, 5.49.

Found: C, 54.12; H, 5.99; N, 5.49.

EXAMPLE 87

Oxalyl chloride (0.06 ml) was added to a solution of 5,6-dimethoxy-3-(3,4-dimethoxyphenyl)indole-2-carboxylic acid (0.2 g) and N,N-dimethylformamide (1 drop) in tetrahydrofuran (10 ml) and stirred for 30 minutes at room temperature. The resulting solution was concentrated under reduced pressure. The residue was dissolved in tetrahydrofuran (5 ml). The tetrahydrofuran solution was added to a solution of diethyl 4-aminobenzylphosphonate (0.204 g) and triethylamine (0.09 ml) in tetrahydrofuran (10 ml). The reaction mixture was stirred for 2 hours at room temperature, poured into water and extracted with chloroform. The chloroform layer was successively washed with water, sodium hydrogen carbonate saturated aqueous solution, water, 2N-HCl and water, dried (MgSO$_4$) and concentrated. The precipitated crystals were collected by filtration and recrystallized from ethyl acetate to give N-[4-(diethoxyphosphorylmethyl)phenyl-5,6-dimethoxy-3-(3,4-dimethoxyphenyl)indole-2-carboxamide (0.283 g, 87%) as pale yellow prisms.

mp: 213°–215° C.

Elementary Analysis for C$_{30}$H$_{35}$N$_2$O$_8$P.½H$_2$O: Calc.: C, 60.91; H, 6.13; N, 4.74. Found C, 61.07; H, 6.17; N, 4.45.

EXAMPLES 88–90

Compounds listed in Table 6 were obtained by the same manner as in Example 87.

Elementary Analysis for C$_{30}$H$_{35}$N$_2$O$_8$P.½H$_2$O: Calc.: C, 60.91; H, 6.11; N, 4.74. Found: C, 61.07; H, 6.17; N, 4.45.

EXAMPLES 88–90

Compounds listed in Table 6 were obtained by the same manner as in Example 87.

TABLE 6

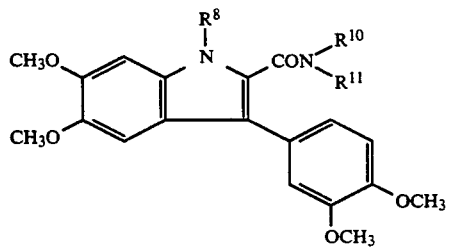

| No. of Example | R⁸ | R¹⁰ | R¹¹ | Yield (%) | MP (°C.) | Solvent for recrystallisation |
|---|---|---|---|---|---|---|
| 88 | H | H | —C₆H₄—P(O)(OC₂H₅)₂ | 70 | 191–192 | ethyl acetate |
| 89 | H | H | —(CH₂)₂P(O)(OC₂H₅)₂ | 60 | 176–177 | ethyl acetate |
| 90 | Et | H | —C₆H₄—Cl | 65 | 195–196 | ether |

EXAMPLE 91

A solution of boron tribromide (BBr₃) (0.18 ml) in dichloromethane (0.36 ml) was dropwise added to a solution of methyl 3-(4-methoxyphenyl)-5,6-dimethylindole-2-carboxylate (0.3 g) in dichloromethane (10 ml) at 0° C. The reaction mixture was stirred for 2 hours at the same temperature, poured into water and extracted with ethyl acetate. The ethyl acetate layer was washed with water, dried (MgSO₄) and concentrated. The precipitated crystals were collected by filtration and recrystallized from acetone to give methyl 3-(4-hydroxyphenyl)-5,6-dimethylindole-2-carboxylate (0.127 g, 44%) as colorless needles.

mp: 247°–248° C.

Elementary Analysis for $C_{18}H_{17}NO_3$: Calc.: C, 73.20; H, 5.80; N, 4.74. Found: C, 72.98; H, 5.91; N, 4.68.

EXAMPLES 92–98

Compounds listed in Table 7 were obtained by the same manner as in Example 91.

TABLE 7

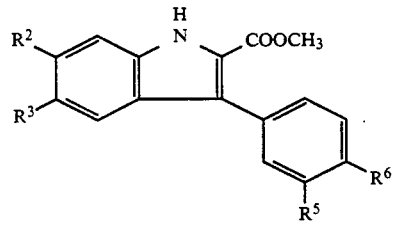

| No. of Examples | Starting Compound (No. of Examples) | R² | R³ | R⁵ | R⁶ | Yield (%) | MP (°C.) | Solvent for recrystallization |
|---|---|---|---|---|---|---|---|---|
| 92 | 26 | H | OH | CH₃ | CH₃ | 45 | 192–193 | acetone |
| 93 | 15 | CH₃ | CH₃ | OH | OH | 40 | 212–214 | acetone |
| 94 | 1 | OH | OH | CH₃ | CH₃ | 63 | 179–180 | acetone |
| 95 | 3 | OH | OH | H | OH | 89 | 256–257 | acetone |
| 96 | 2 | OH | OH | OH | OH | 85 | 288–290 | ether |
| 97 | 14 | —O(CH₂)₂O— | | OH | OH | 80 | 257–258 | acetone-ether |
| 98 | 24 | —O(CH₂)₂O— | | H | OH | 80 | 262–263 | ether |

EXAMPLE 99

Potassium carbonate (0.701 g) and ethyl iodide (0.42 ml) were added to a solution of methyl 5,6-dihydroxy-3-(3,4-dihydroxyphenyl)indole-2-carboxylate (0.2 g) in N,N-dimethylformamide (10 ml). The mixture was stirred at room temperature overnight, poured into water and extracted with ethyl acetate. The ethyl acetate layer was washed with water, dried (MgSO₄) and concentrated. The residue was subjected to a silica gel column chromatography, eluting with ethyl acetate-hexane (1:4, v/v) to give methyl 5,6-diethoxy-3-(3,4-diethoxyphenyl)indole-2-carboxylate. Recrystallization from ether-isopropylether gave cololess prisms (0.131 g, 48%).

mp: 134°–135° C.
Elementary Analysis for $C_{24}H_{29}NO_6$: Calc.: C, 67.43; H, 6.84; N, 3.28. Found: C, 67.20; H, 7.01; N, 3.10.

EXAMPLES 100–104

Compounds listed in Table 8 were obtained by the same manner as in Example 99.

EXAMPLE 111

N,N-Dimethylformamide (3 drops) and oxalyl chloride (0.59 ml) were added to a solution of 5,6-dimethoxy-3-(3,4-dimethoxyphenyl)indole-2-carboxylic acid (2.0 g) in tetrahydrofuran (50 ml). The mixture was stirred for an hour at room temperature and concen-

TABLE 8

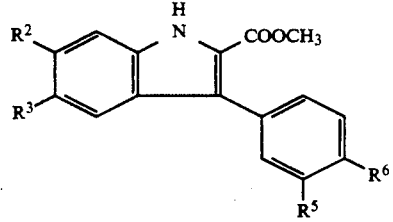

| No. of Examples | Starting Compound (No. of Examples) | $R^2$ | $R^3$ | $R^5$ | $R^6$ | Yield (%) | MP (°C.) | Solvent for recrystallization |
|---|---|---|---|---|---|---|---|---|
| 100 | 95 | $OC_2H_5$ | $OC_2H_5$ | H | $OC_2H_5$ | 36 | 138–139 | isopropyl ether-hexane |
| 101 | 97 | —$O(CH_2)_2O$— | | $OC_2H_5$ | $OC_2H_5$ | 51 | 241–242 | acetone |
| 102 | 97 | —$O(CH_2)_2O$— | | $OCH(CH_3)_2$ | $OCH(CH_3)_2$ | 17 | 222–223 | methanol |
| 103 | 98 | —$O(CH_2)_2O$— | | H | $OC_2H_5$ | 59 | 232–233 | acetone-ether |
| 104 | 98 | —$O(CH_2)_2O$— | | H | $OCH(CH_3)_2$ | 53 | 250–252 | acetone |

EXAMPLE 105

Potassium carbonate (0.139 g) and ethyl iodide (0.13 ml) were added to a solution of 5,6-dimethoxy-3-(3,4-dimethoxyphenyl)indole-2-carboxylic acid (0.3 g) in N,N-dimethylformamide (5 ml). The mixture was stirred for 3 hours at room temperature, poured into water and extracted with ethyl acetate. The ethyl acetate layer was washed with water, dried (MgSO₄) and concentrated. The precipitated crystals were collected by filtration and recrystallized from ethanol to give ethyl 5,6-dimethoxy-3-(3,4-dimethoxyphenyl)indole-2-carboxylate (0.272 g, 84%) as pale red prisms.

mp: 171°–172° C.
Elementary Analysis for $C_{21}H_{23}NO_6$ Calc.: C, 65.44; H, 6.01; N, 3.63. Found: C, 65.54; H, 6.10; N, 3.62.

EXAMPLES 106–110

Compounds listed in Table 9 were obtained by the same manner as in Example 105.

trated under reduced pressure. The residue was dissolved in benzene (20 ml). This benzene solution was added to a solution of tert-butanol (0.79 ml) and N,N-dimethylaniline (0.85 ml) in benzene (30 ml), followed by stirring overnight at room temperature. The mixture was successively washed with water, sodium hydrogen carbonate saturated aqueous solution and water, dried (MgSO₄) and concentrated. The precipitated crystals were collected by filtration and recrystallized from acetone to give tert-butyl 5,6-dimethoxy-3-(3,4-dimethoxyphenyl)indole-2-carboxylate (1.61 g, 70%) as colorless prisms.

mp: 185°–186° C.
Elementary Analysis for $C_{23}H_{27}NO_6$: Calc.: C, 66.81; H, 6.58; N, 3.39. Found: C, 66.96; H, 6.67; N, 3.40.

Study on Bone Resorption Inhibition

Bone resorption inhibiroty activity was determined according to the method of Raisz [Journal of Clinical Investigation (J. Clin. Invest.) 44, 103–116 (1965)].

TABLE 9

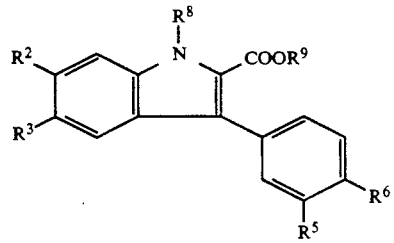

| No. of Examples | $R^2$ | $R^3$ | $R^5$ | $R^6$ | $R^8$ | $R^9$ | Yield (%) | MP (°C.) | Solvent for recrystallization |
|---|---|---|---|---|---|---|---|---|---|
| 106 | $CH_3O$ | $CH_3O$ | $CH_3O$ | $CH_3O$ | H | $(CH_3)_2CH$ | 81 | 147–148 | ether |
| 107 | —$O(CH_2)_2O$— | | $CH_3O$ | $CH_3O$ | H | $C_2H_5$ | 79 | 213–214 | acetone-ethanol |
| 108 | —$O(CH_2)_2O$— | | $CH_3O$ | $CH_3O$ | H | $(CH_3)_2CH$ | 71 | 190–191 | ether |
| 109 | $CH_3O$ | $CH_3O$ | $CH_3O$ | $CH_3O$ | $C_2H_5$ | $C_2H_5$ | 83 | 125–126 | methanol |
| 110 | $CH_3O$ | $CH_3O$ | $CH_3O$ | $CH_3O$ | $C_2H_5$ | $(CH_3)_2CH$ | 80 | 124–125 | methanol |

Thus, a Sprague-Dawley rat at day 19 of pregnancy was subcutaneously dosed with 50 μCi of $^{45}$Ca (a radioisotope of calcium, in CaCl$_2$). On the next day, the animal was laparotomized and the fetuses were removed aseptically. The right and left humeri (radii and ulnae) of each rat fetus were dissected from the body under the dissection microscope. The connective tissue and cartilages were removed as far as possible to prepare bone culture specimens. Each piece of bone was incubated in 0.6 ml of BGJ$_b$ medium (Fitton-Jackson modification [the tradename owned by GIBCO Laboratories, U.S.A.]) containing 2 mg/ml of bovine serum albumin at 37° C. for 24 hours. Then, incubation was carried out for additional two days in the above-mentioned medium. The radioactivities of $^{45}$Ca in the culture medium and bone were determined and the ratio (%) of $^{45}$Ca released from the bone to the medium was calculated according to the following formula.

$$A = \frac{B}{B + C} \times 100$$

A = ratio (%) of $^{45}$Ca released from the bone to the medium
B = $^{45}$Ca count in the medium
C = $^{45}$Ca count in the bone The bones from the fetuses of the same litter were similarly incubated without addition of the test compound for two days and served as controls.

The values for 5 bones per group were expressed in mean. The ratio (%) of this value for the treatment group to the control value was determined. The results are shown in Table 10.

TABLE 10

| Compounds Example No. | $^{45}$Ca discharge (% to control) | |
|---|---|---|
| | 10 μg/ml (conc. of specimen) | 1 μg/ml (conc. of specimen) |
| 1 | 52*** | |
| 3 | 44*** | 54*** |
| 7 | 54** | 75* |
| 9 | 56** | |
| 10 | 52** | |
| 11 | 53*** | 41*** |
| 20 | 56*** | |
| 24 | 58*** | 55** |
| 26 | 59* | |
| 28 | 46*** | |
| 45 | 59*** | 69** |
| 53 | 77*** | |
| 77 | 52*** | 51** |
| 78 | 57* | 37*** |
| 84 | 59*** | |
| 89 | 74* | |
| 97 | 46*** | 60** |
| 98 | 47*** | |
| 100 | 47*** | 71* |

*** $p < 0.001$,
** $p < 0.01$
* $p < 0.05$

As is apparent from Table 10, the compounds (I) possess excellent activity for inhibiting bone resorption. Accordingly, the compound (I) can be used as an inhibitor for bone resorption for mammals (e.g., mouse, rat, rabbit, dog, cat, cow, pig and human being).

The compounds of the invention can be administered to human being through any of oral or parenteral route.

Compositions for oral administration may be solid or liquid forms, specifically tablets (including sugar coated tablets and film coated tablets), pills, granules, powders, capsules (including soft capsules), syrups, emulsions and suspensions. Such compositions will contain conventional carriers or excipients and can be prepared by known methods. Examples of the carriers or excipients for tablets are lactose, starch, sucrose and magnesium stearate.

Compositions for parenteral administration are e.g., injections and suppositories, the former of which includes subcutaneous, intracutaneous, intramuscular or like injections. Such injections can be prepared by suspending or emulsifying the compound (I) in or with sterile aqueous or oily liquids which are usually employed in injections, in accordance with the methods known in the art. Examples of the aqueous liquids for injections are physiological saline and isotonic solution, which may be used together with a suitable suspending agent such as sodium carboxy methylcellulose or a nonionic surfactant upon circumstances. Examples of the oily liquids are sesame oil and soybean oil, which may be used together with a solubilizing agent such as benzyl benzoate or benzyl alcohol. The injections thus prepared are usually put into ampoules.

The oral dosage of the compound (I) or a salt thereof when used as therapeutic agent for an inhibitor for bone resorption is 1 to 500 mg/day, preferably 10 to 150 mg/day for an adult.

PREPARATION EXAMPLE 1

| Tablets | |
|---|---|
| Components of a tablet | |
| (1) Compound of Example 2 | 50.0 mg |
| (2) Cornstarch | 30.0 mg |
| (3) Lactose | 113.4 mg |
| (4) Hydroxypropyl cellulose | 6.0 mg |
| (5) Water | (0.03 ml) |
| (6) Magnesium stearate | 0.6 mg |
| Total | 200.0 mg |

The components (1), (2), (3) and (4) were mixed. After adding water, the mixture was kneaded, dried under vacuum for 16 hours at 40° C. and grounded in a mortar. The resultant was sieved through a 16-mesh sieve to give granules. The component (6) was added to the granules and mixed. The resulting mixture was made to tablets of 200 mg per tablet, using a rotary-type tablet machine (Kikusui Seisakusho in Japan).

PREPARATION EXAMPLE 2

| (1) Compound of Example 14 | 50.0 mg |
|---|---|
| (2) Cornstarch | 30.0 mg |
| (3) Lactose | 113.4 mg |
| (4) Hyroxypropyl cellulose | 6.0 mg |
| (5) Water | (0.03 ml) |
| (6) Magnesium stearate | 0.6 mg |
| (7) Cellulose acetate phthalate | 10.0 mg |
| (8) Acetone | (0.2 ml) |
| Total | 210.0 mg |

From the components (1), (2), (3), (4), (5) and (6), tablets were prepared by the same method as in Preparation Example 1. These tablets were film-coated by use of a solution of the component (7) in acetone in a bar coater (Freunt Co., Ltd.) to give entric coated tablets of 210 mg per tablet.

PREPARATION EXAMPLE 3

| Component of a capsule | |
|---|---|
| (1) Compound of Example 45 | 30.0 mg |
| (2) Cornstarch | 40.0 mg |
| (3) Lactose | 74.0 mg |
| (4) Hydroxypropyl cellulose | 6.0 mg |
| (5) Water | (0.02 ml) |
| Total | 150.0 mg |

The components (1), (2), (3) and (4) were mixed, to which water was added. The mixture was kneaded, dried under vacuum for 16 hours at 40° C. and grounded in a mortar. The resultant was sieved through a 16-mesh sieve to give granules. The granules were packed in No. 3 gelatin capsules with a capsule packing machine (Zanassi Italy) to obtain capsules.

PREPARATION EXAMPLE 4

| Component of a capsule | |
|---|---|
| (1) Compound of Example 48 | 5.0 mg |
| (2) Sodium salicylate | 50.0 mg |
| (3) Sodium chloride | 180.0 mg |
| (4) Sodium metabisulfite | 20.0 mg |
| (5) Methylparaben | 36.0 mg |
| (6) Propylparaben | 4.0 mg |
| (7) Distilled water for injection | (2.0 ml) |
| Total | 295.0 mg |

The components (2), (3), (4), (5) and (6) were dissolved in about one half of the above-mentioned volume of distilled water under stirring at 80° C. The solution thus obtained was cooled to 40° C., to which the compound of the present invention was dissolved. The remaining distilled water was added to the solution so that a final volume can be obtained. The resultant was sterilized through an appropriate filter paper, to give the injection.

The compounds of the present invention possess excellent activity for inhibiting bone resorption and improve bone metabolism by directly working on bones. Accordingly, the compounds of the present invention can be used as a therapeutic agent for osteoporosis.

What we claim is:

1. An agent for inhibiting bone resorption, which comprises a therapeutically effective amount of an indole compound of the formula (I):

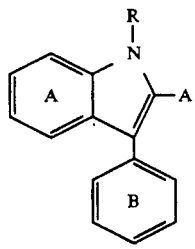

wherein each of the rings A and B may be optionally substituted with one to four substituents selected from the group consisting of:
a. a halogen;
b. $C_{1-10}$ alkyl which is unsubstituted or substituted by a halogen, nitro, amino (which may be substituted by a carboxylic $C_{1-6}$ acyl, $C_{1-10}$ alkyl, iminomethyl, imino(aryl-substituted)methyl, amidino and/or amino), phosphoryl, $C_{1-4}$ alkoxyphosphoryl, sulfo, cyano, hydroxy, carboxy, hydrazino, imino, amidino, carbamoyl, aryl (which may be substituted with a halogen, $C_{1-10}$ alkyl, $C_{1-4}$ alkoxy, $C_{1-10}$ alkylamino, amino, carbamoyl, sulfo, $C_{1-10}$ alkylsulfonyl, cyano, hydroxy, carboxy, nitro, $C_{1-6}$ acyloxy, arylalkyloxy, phosphonyl, $C_{1-4}$ alkoxyphosphoryl and/or sulfoxyl), pyridine, pyridazine, thiazole, oxazole or morpholine (which may be substituted by nitro, oxo, aryl, $C_{2-10}$ alkenylene, halogeno $C_{1-10}$ alkyl, $C_{1-10}$ alkyl sulfonyl, $C_{1-10}$ alkyl, $C_{1-4}$ alkoxy, $C_{1-10}$ alkylamino, amino, halogen, carbamoyl, $C_{1-10}$ hydroxy, cyano, carboxy, phosphonyl, $C_{1-4}$ alkoxyphosphoryl and/or sulfo), wherein the aryl in the above moiety or groups is phenyl or naphthyl;

c. phenyl, naphthyl, biphenyl, anthryl or indenyl which is unsubstituted or substituted by a halogen, nitro, cyano, amino (which may be substituted by a $C_{1-10}$ alkyl, $C_{2-10}$ alkenyl, $C_{3-6}$ cycloalkyl, phenyl and/or naphthyl, phosphoryl, sulfo, hydroxy, sulfoxy, sulfamoyl, $C_{1-10}$ alkyl (which may be substituted by an amino, halogen, hydroxy, cyano and/or $C_{1-4}$ alkoxyphosphoryl), $C_{1-4}$ alkoxy, benzyloxy, phenethyloxy, phenylpropyloxy, $C_{1-10}$ alkylsulfonamido, methylenedioxy, $C_{1-4}$ alkoxyphosphoryl, $C_{1-10}$ alkylsulfonyl, $C_{1-10}$ alkylsulfonylamino, or which may form a condensed ring together with a $C_{3-6}$ cycloalkyl;

d. $C_{2-10}$ alkenyl, which is unsubstituted or substituted by a $C_{1-6}$ alkyl (said $C_{1-6}$ alkyl group optionally being substituted by the substituents for the $C_{1-10}$ alkyl group), halogen, nitro, amino (which may be substituted by a carboxylic $C_{1-6}$ acyl, iminomethyl, amidino, $C_{1-10}$ alkyl and/or aryl), phosphoryl, sulfo, cyano, hydroxy, carboxy, $C_{1-10}$ alkyloxycarbonyl, carbamoyl, $C_{1-10}$ alkylthio, arylthio, $C_{1-10}$ alkylsulfinyl, arylsulfinyl, $C_{1-4}$ alkylphosphoryl, $C_{1-10}$ alkylsulfonyl, arylsulfonyl, sulfamoyl, aryl or carboxylic $C_{1-6}$ acyl, and which includes the E or Z form isomers with respect to the double bond of the $C_{2-10}$ alkenyl group; wherein the aryl in the above moiety or groups is phenyl or naphthyl; and e. hydroxy which is unsubstituted or substituted by a $C_{1-10}$ alkyl, $C_{2-10}$ alkenyl, phenyl-$C_{1-4}$ alkyl, carboxylic $C_{2-4}$ acyl, carboxylic $C_{2-4}$ phenoxy, or a 4-chlorophenoxy;

R is hydrogen, $C_{1-6}$ straight chain, branched-chain or cyclic alkyl or an acyl group formed by combining a $C_{1-6}$ alkyl group with a carbonyl group; and A is a hydroxymethyl group, an esterified carboxyl group in which the ester residue is a straight-chain, branched-chain or cyclic alkyl having 1 to 6 carbon atoms or an aralkyl having 7 to 15 carbon atoms, or an amidated carboxyl group formed by combining a carboxyl group with an amino group which is unsubstituted or substituted by the alkyl, aryl or alkenyl substituents defined as substituents for rings A and B, or by a 5-7 membered heterocyclic group for rings A and B, or by a 2-pyridyl, 3-pyridyl, 4-pyridyl, pyrimidyl, pyrazinyl, pyridazinyl, pyrazolyl, imidazolyl, thiazolyl, isothiazolyl, oxazolyl, isoxazolyl, pyrido)2,3-d)pyrimidyl, benzopyranyl, 1,8-naphthyridyl, 1,5-naphthyridyl, 1,6-naphthyridyl, 1,7-naphthyridyl, quinolyl, thieno(2,3- b) pyridyl, tetrazolyl, thiadiazolyl, oxadiazolyl, triazinyl, triazolyl, thienyl, pyrrolyl, pyrrolinyl, furyl, pyrrolindinyl, benzothienyl, indolyl, imidazolidinyl, piperidyl, piperidino, piperazinyl, morpholinyl or morpholino group which may be substituted by a substituent selected from the group consisting of an amino (which may be substituted by a (1) $C_{1-6}$ acyl, halogen, phenyl and/or $C_{1-10}$ alkyl), (2) halogen, (3) nitro, (4) sulfo, (5) cyano, (6) hydroxy, (7) carboxy, (8) oxo, (9) thioxo, (10) $C_{1-10}$ alkyl (which may be substituted by a phenyl, naphthyl, halogen, amino, hydroxy, carboxy, $C_{1-4}$ alkoxy, $C_{1-10}$ alkylsulfonyl and/or di-$C_{1-10}$ alkylamino), (11) $C_{3-6}$ cycloalkyl, (12) $C_{1-4}$ alkoxy (which may be substituted by a halogen and/or hydroxy), (13) $C_{1-4}$ acyl and (14) phenyl or naphthyl (which may be substituted by a halogen, nitro, $C_{1-10}$ alkyl, $C_{1-4}$ alkoxy, amino, sulfo, hydroxy and/or cyano) group;

or its pharmaceutically acceptable salt, and a pharmaceutically acceptable carrier, diluent or excipient.

2. An indole compound of the formula (I'):

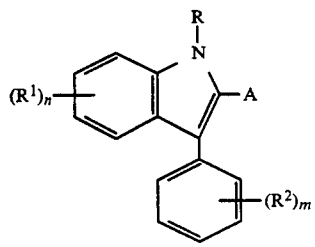

(I')

wherein $R^1$ and $R^2$ can be the same or different and are selected from the group consisting of:
a. hydroxy which is unsubstituted or substituted by $C_{1-10}$ alkyl, $C_{2-10}$ alkenyl, phenyl-$C_{1-4}$ alkyl, carboxylic $C_{2-4}$ acyl or aryl; and
b. a halogen;
or two of each of $R^1$ and $R^2$ may be a bivalent hydrocarbon residue or alkylenedioxy group which form a condensed ring system together with the ring to which they are attached;
R is hydrogen, $C_{1-6}$ straight chain, branched-chain or cyclic alkyl or an acyl group formed by combining a $C_{1-6}$ alkyl group with a carbonyl group; and
A is a hydroxymethyl group, an esterified carboxyl group in which the ester residue is a straight-chain, branched-chain or cyclic alkyl having 1 to 6 carbon atoms or an aralkyl having 7 to 15 carbon atoms, or an amidated carboxyl group formed by combining a carboxyl group with an amino group which is unsubstituted or substituted by the alkyl, aryl or alkenyl substituents defined as substituents for rings A and B, or by a 2-pyridyl, 3-pyridyl, 4-pyridyl, pyrimidyl, pyrazinyl, pyridazinyl, pyrazolyl, imidazolyl, thiazolyl, isothiazolyl, oxazolyl, isoxazolyl, pyrido(2,3-d)pyrimidyl, benzopyranyl, 1,8-naphthyridyl, 1,5-naphthyridyl, 1,6-naphthyridyl, 1,7-naphthyridyl, quinolyl, thieno(2,3-b)pyridyl, tetrazolyl, thiadiazolyl, oxadiazolyl, triazinyl, triazolyl, thienyl, pyrrolyl, pyrrolinyl, furyl, pyrrolindinyl, benzothienyl, indolyl, imidazolidinyl, piperidyl, piperidino, piperazinyl, morpholinyl or morpholino group which may be substituted by a substituent selected from the group consisting of an amino (which may be substituted by a (1) $C_{1-6}$ acyl, halogen, phenyl and/or $C_{1-10}$ alkyl), (2) halogen, (3) nitro, (4) sulfo, (5) cyano, (6) hydroxy, (7) carboxy, (8) oxo, (9) thioxo, (10) $C_{1-10}$ alkyl (which may be substituted by a phenyl, naphthyl, halogen, amino, hydroxy, carboxy, $C_{1-4}$ alkoxy, $C_{1-10}$ alkylsulfonyl and/or di-$C_{1-10}$ alkylamino), (11) $C_{3-6}$ cycloalkyl, (12) $C_{1-4}$ alkoxy (which may be substituted by a halogen and/or hydroxy), (13) $C_{1-4}$ acyl and (14) phenyl or naphthyl (which may be substituted by a halogen, nitro, $C_{1-10}$ alkyl, $C_{1-4}$ alkoxy, amino, sulfo, hydroxy and/or cyano) group;

and n and m each is an integer of 2 to 4;

or its salt.

3. The agent of claim 1 in which the ring A and/or B in the formula (I) are unsubstituted or substituted by one to four of the optionally substituted hydroxyl or alkyl groups.

4. The agent of claim 1 in which the ring A in the formula (I) is substituted by two methoxy groups or is combined with an alkylenedioxy to form a condensed ring system and the ring B is substituted by two or three methoxy or ethoxy groups or combined with an alkylenedioxy to form a condensed ring system.

5. The agent of claim 1 in which the indole (I) is methyl 5,6-dimethoxy-3-(3,4-dimethoxyphenyl)indole-2-carboxylate, 5,6-dimethoxy-3-(3,4-dimethoxyphenyl)-2-hydroxymethylindole, methyl 3-(3,4-dimethoxyphenyl)-5,6-ethylenedioxyindole-2-carboxylate, 3-(3,4-dimethoxyphenyl)-5,6-ethylenedioxy-2-hydroxymethylindole or methyl 5,6-dimethyoxy-3-(3,4-dimethoxyphenyl)-1-ethylindole-2-carboxylate.

6. The compound of claim 2 in which R is a hydrogen atom or a $C_{1-4}$ straight-chain, branched chain or cyclic alkyl, and A is a carboxyl group substituted by a $C_{1-6}$ straight-chain, branched chain or cyclic alkyl, a carbamoyl group optionally substituted by a $C_{1-6}$ straight-chain, branched chain or cyclic alkyl.

7. The compound of claim 6 in which n is 2 or 3 and $R^1$ is a hydroxyl group substituted by a $C_{1-10}$ alkyl, a $C_{1-10}$ alkyl group or two of $R^1$ are an alkylenedioxy which form a condensed ring system together with the ring to which they are attached; m is 2, 3 or 4 and $R^2$ is a hydroxyl group substituted by a $C_{1-10}$ alkyl, a $C_{1-10}$ alkyl group or two of $R^2$ are an alkylenedioxy which form a condensed ring system together with the ring to which they are attached.

8. The compound of claim 6 which is methyl 5,6-dimethoxy-3-(3,4-dimethoxyphenyl)indole-2-carboxylate, 5,6-dimethoxy-3-(3,4-dimethoxyphenyl)-2-hydroxymethylindole, methyl 3-(3,4-dimethoxyphenyl)-5,6-ethylenedioxyindole-2-carboxylate, 3-(3,4-dimethoxyphenyl)-5,6-ethylenedioxy-2-hydroxymethylindole or methyl 5,6-dimethoxy-3-(3,4-dimethoxyphenyl)-1-ethylindole-2-carboxylate.

9. A process for preparing an indole compound of the formula (I'):

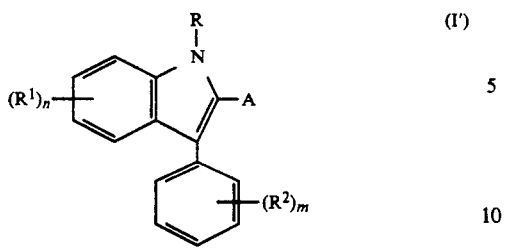

wherein $R^1$ and $R^2$ can be the same or different and are selected from the group consisting of:
a. hydroxy which is unsubstituted or substituted by $C_{1-10}$ alkyl, $C_{2-10}$ alkenyl, phenyl-$C_{1-4}$ alkyl, carboxylic $C_{2-4}$ acyl or aryl; and
b. a halogen;
or two of each of $R^1$ and $R^2$ may be a bivalent hydrocarbon residue or alkylenedioxy group which form a condensed ring system together with the ring to which they are attached;

R is hydrogen, $C_{1-6}$ straight chain, branched-chain or cyclic alkyl or an acyl group formed by combining a $C_{1-6}$ alkyl group with a carbonyl group; and A is a hydroxymethyl group, an esterified carboxyl group in which the ester residue is a straight-chain, branched-chain or cyclic alkyl having 1 to 6 carbon atoms or an aralkyl having 7 to 15 carbon atoms, or an amidated carboxyl group formed by combining a carboxyl group with an amino group which is unsubstituted or substituted by the alkyl, aryl or alkenyl substituents defined as substituents for rings A and B, or by a 2-pyridyl, 3-pyridyl, 4-pyridyl, pyrimidyl, pyrazinyl, pyridazinyl, pyrazolyl, imidazolyl, thiazolyl, isothiazolyl, oxazolyl, isoxazolyl, pyrido(2,3-d)pyrimidyl, benzopyranyl, 1,8-naphthyridyl, 1,5-naphthyridinyl, 1,6-naphthyridinyl, 1,7-naphthyridinyl, quinolyl, thieno(2,3-b)pyridyl, tetrazolyl, thiadiazolyl, oxadiazolyl, triazinyl, triazolyl, thieyl, pyrrolyl, pyrrolinyl, furyl, pyrrolindinyl, benzothienyl, indolyl, imidazolidinyl, piperidyl, piperidino, piperazinyl, morpholinyl or morpholino group which may be substituted by a substituted selected from the group consisting of an amino (which may be substituted by a (1) $C_{1-6}$ acyl, halogen, phenyl and/or $C_{1-10}$ alkyl), (2) halogen, (3) nitro, (4) sulfo, (5) cyano, (6) hydroxy, (7) carboxy, (8) oxo, (9) thioxo, (10) $C_{1-10}$ alkyl (which may be substituted by a phenyl, naphthyl, halogen, amino, hydroxy, carboxy, $C_{1-4}$ alkoxy, $C_{1-10}$ alkylsulfonyl and/or di-$C_{1-10}$ alkylamino), (11) $C_{3-6}$ cycloalkyl, (12) $C_{1-4}$ alkoxy (which may be substituted by a halogen and/or hydroxy), (13) $C_{1-4}$ acyl and (14) phenyl or naphthyl (which may be substituted by a halogen, nitro, $C_{1-10}$ alkyl, $C_{1-4}$ alkoxy, amino, sulfo, hydroxy and/or cyano) group;
and n and m each is an integer of 2 to 4;
or its salt, which comprises:
A. heating, at a temperature of from approximately 10° to approximately 200° C., for a period of from 0.5 to 100 hours, a compound of the formula (II):

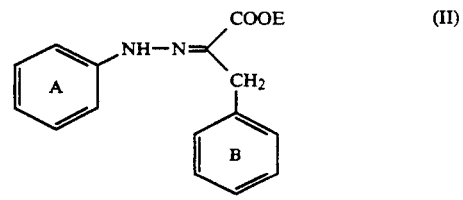

to obtain a compound of the formula (I-1):

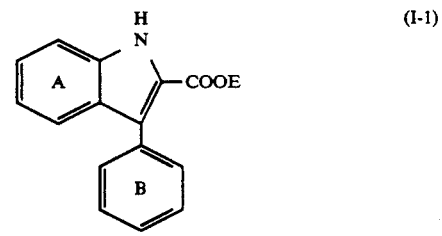

wherein E is an ester residue for the esterified carboxyl, the ring A and ring B have the substituents $(R^1)_n$ and $(R^2)_m$ as in the formula (I'), respectively;

B. reacting a compound of the formula (I-1), at a temperature of from approximately −20° to approximately 100° C., in a solvent, in the presence of a base, with a compound of the formula R-X wherein R has the same meaning as in the formula (I') and X is a leaving group selected from the group consisting of halogens and sulfonyloxys to obtain a compound of the formula (I-2):

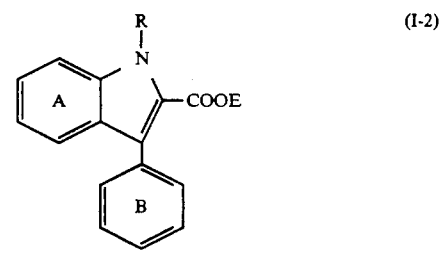

wherein the symbols are as defined above;

C. reducing a compound of the formula (I-2) to obtain a compound of the formula (I-3):

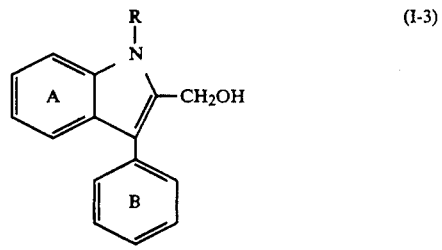

wherein the symbols are as defined above;

D. hydrolyzing a compound of the formula (I-1) or (I-2), at a temperature of from approximately −20° to approximately 150° C., to obtain a compound of the formula (I-1) or (I-2) to obtain a compound of the formula (I-4):

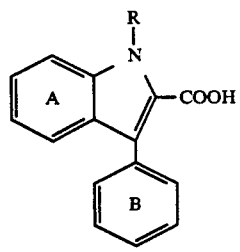

wherein the symbols are as defined above;

E. esterifying a compound of the formula (I-4) to obtain a compound of the formula (I-5):

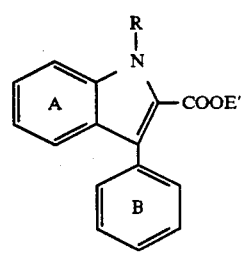

wherein E' has the same meanings as defined for E and the other symbols are as defined above;

F. amidating a compound of the formula (I-4) to obtain a compound of the formula (I-6):

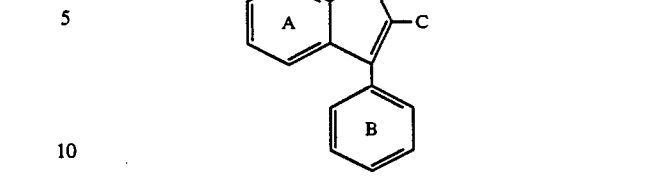

wherein C is an amidated carboxyl group and the other symbols are as defined above;

G. eliminating a substituent in the substituted hydroxyl group of a compound of the formula (I') to obtain a compound of the formula (I') wherein $R^1$ and/or $R^2$ are hydroxyl group; or H. converting a compound of the formula (I') wherein $R^1$ and/or $R^2$ are hydroxyl group into the corresponding compound wherein $R^1$ and/or $R^2$ are a substituted hydroxyl group through alkylation, aralkylation or acylation; and if necessary I. converting a compound of the formula (I') into the corresponding salt.

10. A method of inhibiting bone resorption which comprises administering a therapeutically effective amount of a compound of the formula (I) of claim 1 or its pharmaceutically acceptable salt optionally together with a pharmaceutically acceptable carrier, diluent or excipient to a mammal suffering from bone loss.

11. A method of treating osteoporosis which comprises administering a therapeutic effective amount of a compound of the formula (I) of claim 1 or its pharmaceutically acceptable salt optionally together with a pharmaceutically acceptable carrier, diluent or excipient to a human being suffering from osteoporosis.

* * * * *

UNITED STATES PATENT AND TRADEMARK OFFICE
CERTIFICATE OF CORRECTION

PATENT NO. : 5,296,499

DATED : March 22, 1994

INVENTOR(S) : Takashi SOHDA et al.

It is certified that error appears in the above-identified patent and that said Letters Patent is hereby corrected as shown below:

| | | |
|---|---|---|
| Claim 1<br>Column 28<br>line 66 | pyrido)2,3-d)pyrimidyl | pyrido(2,3-d)pyrimidyl |
| Claim 6<br>Column 30<br>line 40 | $C_{1-4}$ straight chain | $C_{1-6}$ straight chain |

Signed and Sealed this

Twenty-second Day of November, 1994

Attest:

BRUCE LEHMAN

Attesting Officer

Commissioner of Patents and Trademarks